United States Patent [19]

Tennerstedt

[11] Patent Number: 4,935,190

[45] Date of Patent: Jun. 19, 1990

[54] METHOD OF MAKING BALLOON RETENTION CATHETER

[75] Inventor: Milton R. Tennerstedt, Wilmette, Ill.

[73] Assignee: William G. Whitney, Glenview, Ill.

[21] Appl. No.: 71,854

[22] Filed: Jul. 10, 1987

[51] Int. Cl.$^5$ .................... B29C 49/18; B29C 49/64
[52] U.S. Cl. .................................. 264/529; 264/530;
 264/534; 264/535; 264/570
[58] Field of Search ................... 604/96, 271; 128/328;
 264/523, 534, 529, 573, 530, 570

[56] References Cited

U.S. PATENT DOCUMENTS

| 805,851 | 11/1905 | Goldfarb | 604/271 |
|---|---|---|---|
| 4,428,900 | 1/1984 | Riley et al. | 264/573 |
| 4,490,421 | 12/1984 | Levy | 604/96 |
| 4,671,982 | 8/1988 | Snyder | 264/573 |
| 4,820,270 | 4/1989 | Hardcastle et al. | 604/96 |

FOREIGN PATENT DOCUMENTS 0081883  6/1983  European Pat. Off. ............ 264/573

Primary Examiner—Jan H. Silbaugh
Assistant Examiner—Catherine Timm
Attorney, Agent, or Firm—Hill, Van Santen, Steadman & Simpson

[57] ABSTRACT

An expandable section plastic tube having utility, for example, in inflatable balloon section catheters, and a method of making the same. The tube formed of thermoplastic material is inserted in a wall defining member, such as a mold, having an enlarged section surrounding a portion of the tube. The tube portion is then heated to a thermal plastic temperature and is expanded into the enlarged section by a sudden application of pressure resulting in a thinning of the tube wall in the expanded area. Thereafter, the tube is cooled and removed from the mold. In the making of a catheter, one section of the tube to one side of the expanded area is inverted and drawn into the section of the tube on the other side of the expanded area whereby the expanded area forms a balloon end at one end of the telescoped tube sections.

23 Claims, 2 Drawing Sheets

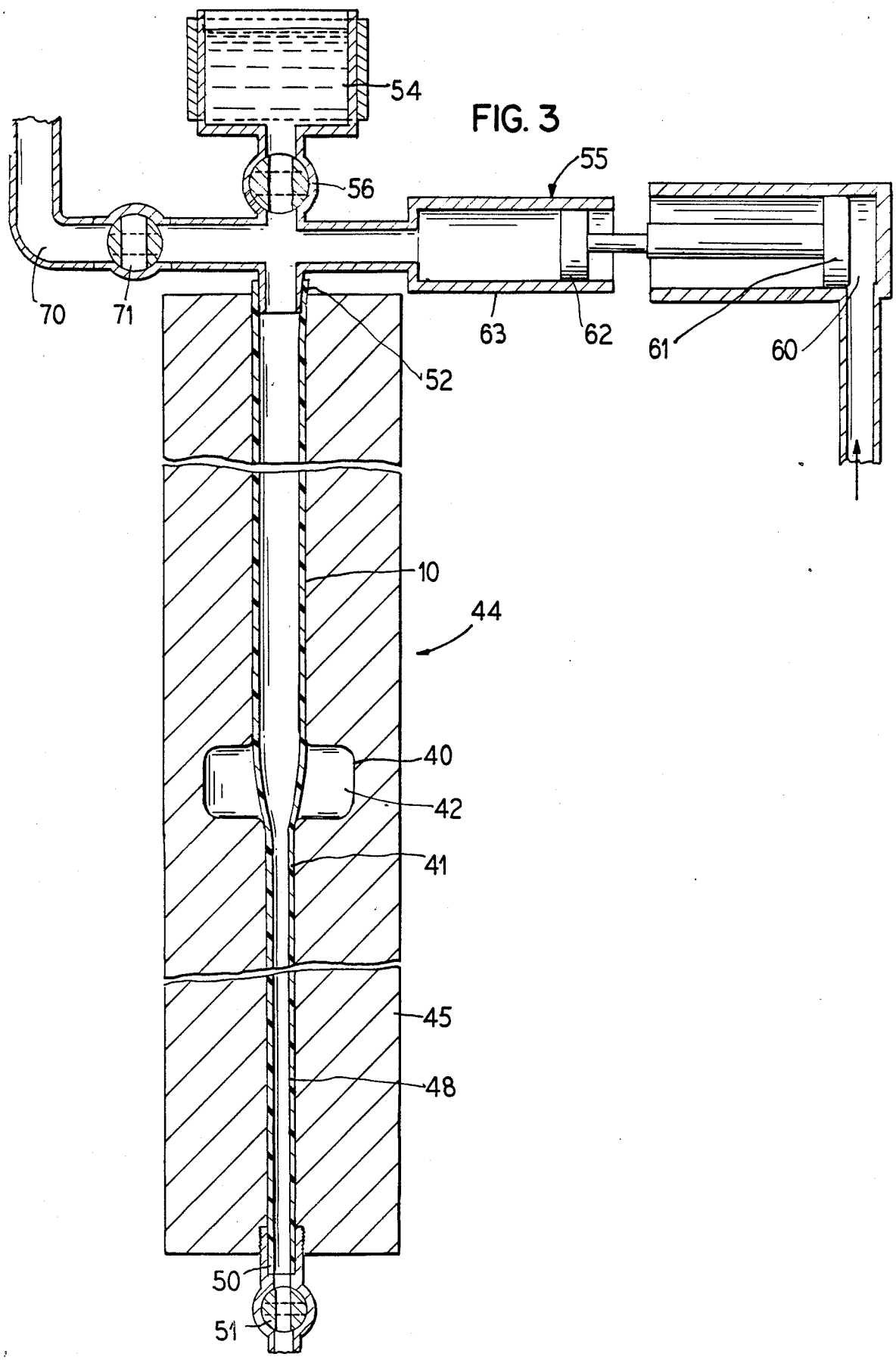

METHOD OF MAKING BALLOON RETENTION CATHETER

BACKGROUND OF THE INVENTION

1. Field of the Invention

This invention relates to expandable section tubes and to methods of making same and more particularly to balloon catheters.

2. Background Information

Tubes having expandable thin walled sections have many known uses, particularly in medicine where such tubes may be used as drainage catheters, plaque compression devices for use in blood vessel treatments, blockage devices for blocking flow through various bodily passageways, irrigation instruments and the like. Typical such devices include catheters of the type generally known as Foley catheters utilizing a dual lumen elastomer catheter having a balloon section adjacent one end. One lumen is directed to the interior of the balloon section formed on an outer wall of the catheter and is used for inflating and deflating the balloon section. Such catheters have known disadvantages in that the addition of a second lumen and the necessary separating walls separating the balloon lumen from the main lumen reduces the cross section dimension of the main lumen. Such devices may be utilized in procedures requiring a maximum lumen diameter in association with a minimum overall outer diameter. Due to the use of dual lumens for a given outer diameter, the main lumen inner diameter is necessarily restricted. Additionally, such known catheters, to the extent that the expandable balloon section is spaced from the distal end, provide disadvantages in that the end section projecting distally of the balloon may interfere with desired procedures, such as drainage, or may provide an irritant in situations where the catheter is left in place for a period of time, such as, for example, when it is used as a long-term bladder drainage device where the bladder wall opposite the catheter may become irritated by the catheter distal tip when the bladder is collapsed.

U.S. Pat. No. 3,050,066 discloses a catheter device which improves upon the Foley type catheter in that the balloon section is located at a distal end of two telescoping tube sections, the balloon section forming a joinder wall between the inner tube and the outer tube such that the annulus between the inner tube and the outer tube provides a communication to the interior of the balloon section for inflation and deflation. In such a device the balloon section is located immediately at the distal end of the catheter. While this construction offers advantages over a Foley type catheter, it is particularly difficult to manufacture and use since it requires a connecting joint to be formed between the connection of one of the inner or outer tube ends and the balloon. This joint, which is used to connect the balloon end to the inner tube when the balloon is formed as a soft expanded section at the end of the outer tube, naturally provides an assembly which is difficult to manufacture and which has an inherent weakness at the joint allowing the possibility of leakage or rupture.

It would therefore be an advance in the art to provide an expandable section tube where the expandable section is formed integrally with portions of the tube extending to both sides of the expandable section and to utilize such tubes in the formation of a balloon catheter having a balloon section located at a terminal distal end of the catheter.

SUMMARY OF THE INVENTION

This invention provides a method of manufacturing expandable section tubes and a catheter formed from such a tube and a method of manufacturing the catheter.

The expandable section of the tube consists of a thin walled expansion to a larger diameter of a section of the tube which is formed in situ by an essentially instantaneous expansion. In the preferred embodiment herein described, the initial tube is formed of a thermoplastic material and may be produced by standard known processes such as extrusion. A section of such thermoplastic tubing is then placed in a mold which confines the tube portions to either side of an intermediate area which is to form the balloon or expanded section. The material of the tube is then heated until at least the intermediate section reaches a thermoformable temperature range. The tube is filled with liquid, which may form part of the heating medium. The liquid is confined and thereafter subjected to a sharp pressure spike. As used herein, the term "pressure spike" signifies the rapid increase in pressure in a semi-confined substantially incompressible fluid with resulting rapid fluid flow into the expanding areas of the tube with substantially equal pressure application at all points of fluid tube contact. The pressure spike expands the intermediate section to form a thin walled expanded diameter section. Subsequent cooling of the tube and removal from the mold provides a completed tube section having a thin walled expanded area.

When the tube is to be used as an inflatable balloon catheter, an end portion is inverted and drawn back through itself, through the thin walled expanded section, and then through the other end portion lying on the other side of the expanded section until the expanded section is provided at the distal end of a catheter length substantially defined by the coaxial tube portions. If desired, the tube portions can then be joined at their proximal ends and the space between them filled with a fluid such as a sterile liquid to be used for inflating the balloon end. In such an instance, the area between the inner tube portion and the outer tube portion becomes the area filled with fluid and the two tube portions may be telescopically movable such that during catheter insertion the entirety of the balloon section is drawn interior of the outer diameter tube portion.

During the forming step, particularly where coaxial tube portion catheters are to be created, one of the tube portions extending from the intermediate balloon area to one side thereof may also be expanded to a larger diameter than the remaining portion to the other side during the same pressure forming operation by receiving the portion to be expanded in a larger diameter mold bore. The thus expanded portion can then be used as the outer catheter tube.

It is therefore an object of this invention to provide an improved method of manufacture of expandable thin walled section tubes.

It is another and more particular object of this invention to provide a method of forming tubes having intermediate sections of larger diameter than remaining sections of the tube, the intermediate section formed by localized expansion of the tube when the tube is in a thermoforming temperature range.

It is another and more particular object of this invention to provide an improved method of forming tubes having intermediate expanded diameter thin walled sections which comprises the steps of providing a thermoplastic tube, confining portions of the tube in a mold with a portion of the mold having a larger diameter section than the outer diameter of the tube, heating the tube to a thermoforming temperature and thereafter providing a sharp pressure spike to the interior of the tube when in the thermoforming temperature range.

It is another particular object of this invention to provide a method of making tubes having expandable balloon sections intermediate opposite ends of the tube which comprises the steps of providing a thermoformable tube, providing a mold having a bore channel for receipt of the tube, the bore channel having at least one enlarged diameter section having a diameter greater than the tube diameter, placing the tube in the mold bore channel, filling the tube with a fluid, heating the tube to a thermoforming temperature, sharply increasing the pressure of the fluid and thereby expanding by fluid flow and pressure a portion of the tube interior of the increased diameter section of the mold bore channel to a diameter greater than the diameter of other portions of the tube and thereafter cooling the tube and removing it from the mold.

It is another general object of this invention to provide an improved balloon catheter.

It is a more specific object of this invention to provide a balloon catheter having an expandable balloon section formed at a distal end of the catheter formed in situ integral with remaining portions of the catheter.

It is another, and particular object of this invention, to provide an improved balloon catheter having coaxial tube sections interconnected together at a distal end by an expandable thin walled balloon section formed integral with both coaxial sections and having means for expanding the balloon section.

Other objects, features and advantages of the invention will be readily apparent from the following description of a preferred embodiment thereof, taken in conjunction with the accompanying drawings, although variations and modifications may be effected without departing from the spirit and scope of the novel concepts of the disclosure, and in which:

DESCRIPTION OF THE DRAWINGS

FIG. 3 is a fragmentary sectional diagrammatic view of a mold assembly for manufacture of expanded wall tubes according to this invention;

DESCRIPTION OF THE PREFERRED EMBODIMENTS

Figure 1:
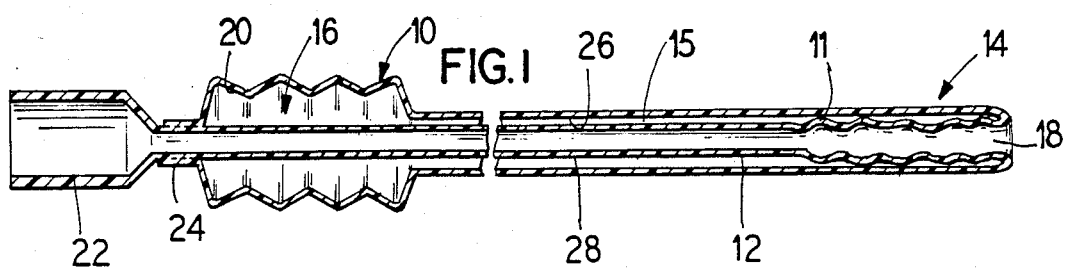
FIG. 1 is a cross-sectional view of a catheter according to this invention.
Figure 2:
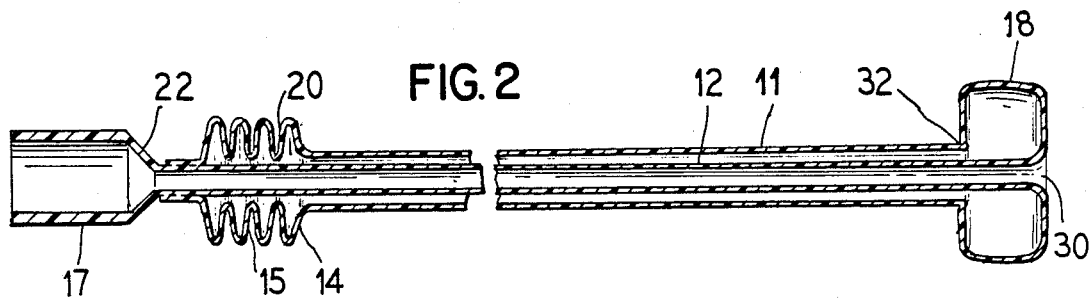
FIG. 2 is a cross-sectional view similar to FIG. 1 showing the catheter of FIG. 1 with the balloon portion expanded.

As best illustrated in FIGS. 1 and 2, this invention provides a catheter 10 consisting of an outer diameter 11 tube portion, an inner diameter 12 tube portion, a proximal end and a distal end 14. The annulus 15 between the inner tube 12 and the outer tube 11 may, if desired, be filled with a fluid 16 such as a sterile liquid. At the distal end 14, the inner 12 and outer 11 tube portions are interconnected through a thin walled expandable balloon section 18 formed integrally with the tube portions 11 and 12. In FIG. 1, the balloon section 18 has been withdrawn entirely within the outer diameter tube portion 11. The outer diameter tube portion 11 may have an enlarged section 20 adjacent its proximal end forming a reservoir for the liquid and the inner diameter tube section may have an integral or attached bulbous proximal end section 22 which projects beyond the reservoir section 20 and which may be used for connection to a drainage tube. The inner and outer tubes are sealingly joined adjacent the proximal ends as at 24 to retain the fluid 16 within the annulus between the tube portions. It will be appreciated that, in the embodiment of FIG. 1, the outer tube portion 11 has an inner diameter 26 which is greater than the outer diameter 28 of the inner tube portion 12 by an amount sufficient to provide an annulus between the tube portions for flow of the fluid 16. The extent of the annulus has been exaggerated in FIG. 1 for clarity.

In the condition shown in FIG. 1, the catheter is configured for insertion into a patient. It will be appreciated that by reason of the fact that the balloon section 18 has been withdrawn entirely within the outer tube portion 11, that the distal end 14 provides a semi-rounded ring having a rigidity determined by the material of the outer tube portion whereas the entire catheter has a rigidity and stiffness determined by the composite of the inner tube portion, the outer tube portion and the fluid between the two tube portions. By controlling wall thickness and material selection, as well as by use of different types of fluids, the flexibility, stiffness, rigidity, collapse resistance and other properties of the catheter may be chosen over a wide range of possibilities. Preferably the catheter of this invention is formed from a thermoformable plastics material such as, for example, polyurethane. Other thermoplastic materials, such as polyethylene and polyvinylchloride can also be used, however, where catheters are provided for medical purposes, polyurethane may be preferred. One consideration in choice of materials is avoidance of blocking, i.e., sticking of the inner tube portion to the outer tube portion. Free sliding is an important consideration in the function of the catheter. Polyurethane with a barium sulfate added has been found to have the desired sliding ability. Other lubricating additives may also work. Inherently slipperly materials such as PTFE may also work well. In some instances, merely increasing the duometer may be adequate. Such thermoformable plastics have advantages over rubbers, such as latex, previously used in catheters in that they are frequently easier to remove from patients' bodies and are less likely to become encrusted with salts and other body debris. This is particularly advantageous where long term indwelling catheters are used, such as for bladder control in paraplegics.

It will be appreciated that the choice of catheter circumference is substantially unlimited by this invention with a wide range of tube sizes being utilizable. Due to the coaxial positioning of the inner and outer tube portions, the lumen of the inner tube can be relatively large with respect to the overall catheter dimension since the axial communication with the balloon section is provided by the entire annulus area surrounding the inner tube portion. This also provides for better fluid flow to the balloon section in those instances where the catheter has been curved or bent in following bodily passageways. Such bends or curves are less likely to block the entire annulus of a catheter according to this invention than prior double lumen balloon catheters where the balloon communicating lumen was kept as small as possible to allow for as large as possible operating lumens.

It will further be appreciated that the lumen of the inner tube portion may be provided for any number of purposes such as irrigation, drainage, suction, instrument passage, medication passage or the like. The proximal end section 22 of the inner tube portion may be variously configured and may be attached to various other tubes or instruments as desired. In fact, the proximal ends of the tube portions, although illustrated in FIG. 1 as being sealed together, may be left free in manufacture for later attachment to other structures or instruments including, for example, valve controlled collars in which instance, the reservoir section 16 is not needed.

In use, the catheter of FIG. 1 is inserted into position in the desired area and the balloon end is then expanded. As shown in FIG. 2, this is accomplished by moving the inner tube portion 12 through the outer tube portion 11 until the distal end 30 of the inner tube portion extends beyond the distal end 32 of the outer tube portion such that the balloon section 18 lies axially beyond the distal end 32. In the embodiment of FIGS. 1 and 2, this can be accomplished merely by restraining movement of the outer tube while pushing against the proximal end section 22 of the inner tube. Because of the entrapped fluid 16 in the reservoir, the reservoir 20 will collapse and the balloon 18 will expand. Use of this design allows predetermined control of maximum balloon size.

FIG. 3 illustrates one type of apparatus for practicing the method of forming an expanded thin walled section of a plastic tube in accordance with this invention. A mold member 40 is provided with a channel bore 41. The mold may be a split half mold with the bore 41 formed as opposed channels in the mating faces of the split halves. A section of the mold 42 is provided with an increased inner diameter channel area intermediate the ends. This increased inner diameter area may be configured as desired. Preferably, the mold portions 44 and 45 lying to either side of the increased diameter section are equipped with channels dimensioned to the size of the initial tube 48. However, if desired one, or both channel bores may have a diameter greater than the initial tube diameter so as to provide for resizing of those portions of the tube formation of the balloon section. In the illustrated embodiment, the mold portion 44 is provided with a channel bore of greater diameter than the mold portion 45. In such instances, either a constant diameter tube may be utilized with the portion of the tube received interior of the mold portion 44 to be expanded during formation of the balloon or, if desired, a varying diameter tube may be provided. Such varying diameter tubes are known and can be produced by known manufacturing techniques.

After the tube 48 has been placed in the mold channel, and the mold closed, one end 50 of the tube may be provided with a valve 51 or a connection to a valved conduit. It will be appreciated that FIG. 3 is a simplified schematic drawing and that many variations on this apparatus will become apparent to those of skill in the art. The other end 52 of the tube is attached to a fluid supply device including a source of fluid 54 and a source of pressure 55. After encapsulation of the tube 48 by the mold, fluid is supplied from the source 54 through valve 56 to fill the tube. When the tube is filled, valve 51 is closed. The tube is then heated to its thermoforming temperature. This can be accomplished either by heating elements within the mold, or by heating of the fluid 54 and introduction of the heated fluid to the interior of the tube or by other means, such as external radiation. When the tube had reached its thermoforming temperature, both valves 51 and 56 are closed and a sharp pressure spike is delivered to the interior of the tube through the fluid filling the tube. In the illustrated embodiment, the pressure spike may be provided by an impact air cylinder assembly 60 connected to a source of pressure air driving a piston 61 operatively connected to a piston 62 of cylinder 63 which is filled with the fluid of the tube.

Since the pressure spike is delivered through the fluid interiorly filling the tube, the pressure transmission will be substantially instantaneous and equal through all portions of the tube. This will cause the heated section of the tube interior of the enlarged diameter section 42 to expand outwardly as a result of fluid dynamics substantially independently of the local elastic properties of the plastic material. The result is a expansion of the area of the tube interior of the enlarged diameter section 42 and the formation of a generally concentric balloon section of substantially uniform wall thickness in normal cross-section.

It has been determined that the expanded balloon section does not have to totally fill the expanded inner diameter portion 42 of the mold and that lesser expansions of the tube may be formed. To this end, proper sizing of the cylinder 63 with respect to the piston position can provide for an accurate dosaging of the fluid movement into the tube during the application of the pressure spike substantially instantaneously increasing pressure of the fluid interior of the tube. In this manner, control of the degree of balloon formation is possible. By using a lesser quantity of fluid displaced by the cylinder 63, a smaller balloon section can be created, while providing a greater quantity of fluid a larger balloon section can be provided.

It will also be appreciated that during this forming step, if the portion of the tube in the portion 44 of the mold is of smaller diameter than the channel diameter, that tube portion can be resized simultaneously with the formation of the balloon section.

After formation of the balloon section, the resultant tube is preferably cooled while remaining within the mold. To accomplish this, valve 51 can be provided with a setting where it will maintain a desired intermediate pressure, and a cooled liquid can be provided through conduit 70 and valve 71 to flow cooled fluid through the tube while maintaining a pressure interior of the tube adequate to continue the distension of the balloon section until it is cooled below its thermoforming temperature.

It will also be appreciated that balloon geometry can be selectively chosen by variously configuring the enlarged diameter section 42 and by expanding the tube into conformity with the interior wall surface of the section 42. This allows for creation of particular geometries of the balloon which may be desired for particular applications. In the same manner, the reservoir 20 could be formed along with the formations of the balloon section or, if desired, the reservoir could be attached later.

Using an apparatus of the type described in connection with FIG. 3, I have formed a thin walled expanded diameter section of a tube. Beginning with a polyurethane tube having a diameter of 0.210" and a wall thickness of 0.018", I heated the tube in the mold to a temperature of approximately 200° F. The pressure spike impact was driven by air pressure of 80 psi directed to an impact piston such as piston 61 having a diameter of 1½" driving a piston in the fluid reservoir cylinder, such as cylinder 63, having a diameter of ¾". The volume of the reservoir 63 was approximately 6 cubic centimeters. The resultant balloon section had good uniformity of cross-sectional wall thickness, good integrity at both ends of the expanded section to the remaining portions of the tube, good retained elasticity and fluid tightness. Expansion of the section occurs in a fraction of a second.

Figure 4:
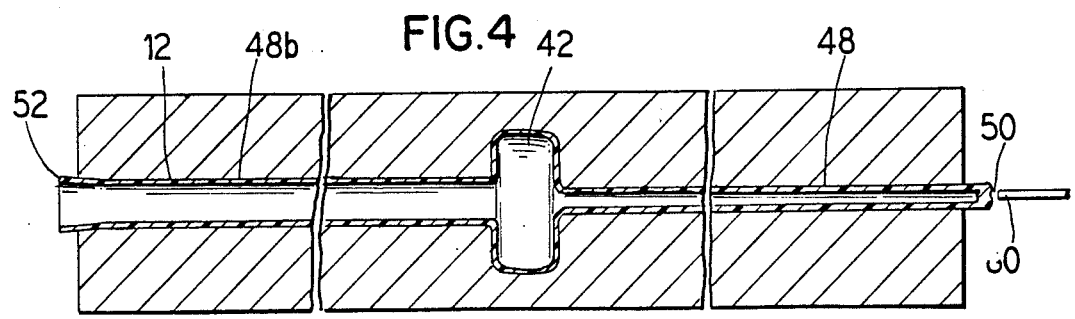
FIG. 4 is a diagrammatic sectional view of a mold and expanded tube just prior to inversion of the tube to form the catheter.
Figure 5:
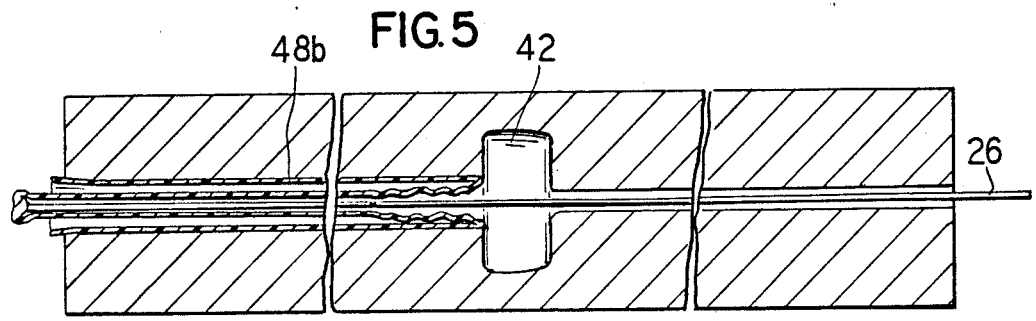
FIG. 5 is a view similar to FIG. 4 illustrating the inverted catheter.

As illustrated in FIGS. 4 and 5, subsequent to formation of the expanded section tube, the tube can be formed into a catheter while still in the mold. By closing off the end 50 of the smaller diameter tube portion 48, pressure can be retained interior of the tube through the end 52. Pressure at this point is relatively low pressure and is for the purpose of maintaining the tube in engagment with the sidewalls of the mold bore channel. Thereafter, a rod or other stiff member 80 can be pushed or pulled against the end 50 to cause the end 50 to turn in upon itself inverting the portion 48 interior of itself. The pressure maintenance at this time allows the tube to be pressed against the channel walls so that the application of pressure by the rod 80 will not cause an axial collapse of the tube but instead will cause it to invert in upon itself. It will of course be appreciated that the end 52 at this time can be equipped with a pressure regulating valve so that as the tube portion 48 is inverted into itself, a desired constant pressure can be maintained and fluid bled to maintain desired pressure. Movement of the rod 80 is continued until, as shown in FIG. 5, tube portion 48a is pushed back through to portion 48b such that tube 48a now becomes the inner tube section 12 and tube portion 48b becomes the outer tube section 11 of the catheter. Preferably, this is continued until the balloon section formed in the expanded diameter cavity 42 is withdrawn into the distal end of tube section 41. It will be appreciated by those skilled in the art that separate expansion and inversion molds may be used, if desired.

It will therefore be appreciated from the above that I have provided an improved method of making expanded diameter thin walled tube portions integral with adjacent smaller diameter tube portions and I have shown how such tubes may be formed into balloon catheters.

Although the teachings of my invention have herein been discussed with reference to specific theories and embodiments, it is to be understood that these are by way of illustration only and that others may wish to utilize my invention in different designs and applications.

I claim as my invention:

1. A method of making an expanded diameter section tube comprising the steps of: providing a hollow tube length formed of thermo-plastics material having a determined maximum outer diameter, providing a mold having a channel means therein, a first portion of which has an inner diameter greater than other portions and greater than the determined maximum outer diameter, inserting the tube length in the channel means with a first portion of the tube interior of the first portion of the channel means, filling the tube with a substantially incompressable liquid applying heat to the tube to elevate the temperature of at least the first portion of the tube interior of the first portion of the channel means to a temperature at which the tube is thermoplastically deformable, thereafter applying an abrupt substantially instantaneous high pressure spike to liquid in the interior of the tube by abruptly forcing a predetermined additional fixed quantity of said substantially incompressible liquid into the tube interior and thereby expanding the first portion of the tube by the resultant pressure spike to a greater outer diameter than the determined maximum outer diameter and thereafter cooling the expanded portion of the tube below the thermoplastic temperature thereof.

2. The method of claim 1, wherein means are provided to confine the liquid during the high pressure applying step.

3. The method of forming a thin-walled expanded portion of a tube length which comprises the steps of providing a tube length of thermoformable plastic, having a determined minimum wall thickness and a maximum outer diameter, providing a mold having a channel therein with a first portion having a larger inner diameter than an outer diameter of a portion of the tube to be expanded, inserting the tube in the mold channel with the portion to be expanded positioned interior of the increased inner diameter first portion of the channel, closing the mold and encasing at least portions of the tube length interior of the mold channel, substantially filling the tube length with a substantially incompressible liquid at a first pressure, heating the tube length to a thermoforming temperature range of the tube, substantially instantaneously sharply increasing the pressure of the liquid interior of the tube to a second pressure to apply a high pressure spike by abruptly forcing a fixed predetermined additional quantity of said liquid into said tube and thereby expanding by liquid pressure at least the portion of the tube interior of the increased inner diameter portion of the channel, maintaining pressure interior of the tube at a third pressure while cooling the tube to a temperature below the thermoforming temperature of the tube.

4. The method of claim 3, wherein the second pressure is higher than the first pressure.

5. The method of claim 4, wherein the third pressure is lower than the second pressure.

6. The method of claim 5, wherein heating of the tube is accomplished by heating the liquid.

7. The method of claim 6, wherein cooling of the tube is accomplished by a cooling fluid within the tube, the cooling fluid being maintained at the third pressure.

8. A method of manufacture of a balloon catheter comprising the steps of providing a hollow tube length formed of thermoplastic material having a wall thickness, providing a mold having a channel therein dimensioned for receipt of the tube length and having an increased diameter section of substantially greater inner diameter than the outer diameter of a portion of the tube length to be received therein, inserting the tube in the channel with a first portion of the tube received interior of the increased diameter portion of the channel, filling the tube interior with a substantially incompressible fluid, elevating the temperature of the tube to a thermoforming temperature range of the tube material, substantially instantaneously increasing pressure of the fluid interior of the tube to apply a high pressure spike by abruptly forcing a fixed predetermined additional quantity of said liquid into said tube and thereby expanding the tube portion interior of the increased diameter portion of the channel by stretching and thinning the wall thickness of the tube portion, thereafter reducing the pressure of the fluid while maintaining the fluid at a greater than atmospheric pressure, cooling the tube to a temperature below the thermoforming temperature range, and thereafter withdrawing the tube length from the mold.

9. The method of claim 8, wherein the tube length has end portions positioned within a mold extending to either side of the increased diameter section of such mold and wherein subsequent to cooling, one of said end portions is inverted and drawn back interiorly of the expanded section and interiorly of the other portion.

10. The method of claim 9, wherein the one portion of the tube length has an inverted outer diameter less than the inner diameter of the other portion.

11. The method of claim 10, wherein the inversion and withdrawing of the one portion is continued until the expanded portion is drawn interiorly of the other portion.

12. The method of claim 10, wherein the step of inverting the withdrawing is performed while the tube length is in the mold.

13. The method of claim 12, wherein the step of inverting and withdrawing is performed while maintaining a pressure interior of the tube length sufficient to cause the outer diameter of the tube length to be pressed into contact with an inner diameter surface of the mold channel.

14. The method of claim 9, wherein separate molds are used for expanding the tube and inverting the tube.

15. The method of making an expanded diameter section tube comprising the steps of: (A) providing a mold having a molding channel bore therein with first and second spaced apart axial ends and an intermediate area positioned between the ends, the intermediate area having an inner diameter greater than other sections of the bore, (B) providing a hollow tube length formed of thermoplastics material, (C) inserting the tube length in the bore with a portion thereof in the intermediate area, (D) substantially filling the interior of the tube with a substantially incompressible liquid, (E) increasing the temperature of the tube until at least the portion of the tube in the intermediate area reaches a thermoplastic temperature range, (F) substantially instantaneously sharply increasing the pressure of the fluid interior of the tube to apply a high pressure spike by abruptly forcing a fixed predetermined additional quantity of said liquid into said tube and thereby expanding the portion of the tube in the intermediate area while stretching and thinning the wall thickness of the expanded portion, and (G) thereafter cooling the tube in the mold.

16. The method of claim 15, wherein the molding channel bore has a greater diameter between the first end and the intermediate area than between the intermediate area and the second end.

17. The method of claim 16, wherein the tube length portion between the first end and the intermediate area is expanded in diameter during step F.

18. The method of claim 15, wherein the expanded portion in the intermediate area is flexible subsequent to step G.

19. The method according to claim 18, including the steps of: (H) inverting the portion of the tube length at the second end and moving the second end back along the tube length interior thereof through the expanded portion of the tube in the intermediate area thence through the portion of the tube from the first end to the intermediate area until the portion of the tube from the intermediate area to the second end is positioned interior of the portion of the tube from the first end to the intermediate area.

20. The method of claim 19, including the step of maintaining an interior pressure in said tube during said inverting step.

21. The method of claim 20, wherein the expanded portion in the intermediate area is collapsed and drawn into the interior of the tube length from the first axial end to the intermediate area.

22. The method of making an expanded diameter section tube comprising the steps of:
(a) Providing an mold means having a tube retaining means therein with an intermediate portion intermediate axial ends of the mold means and having a diameter greater than axial lengths of the mold means positioned between the greater diameter portion and the axial ends thereof; (b) providing a hollow tube length formed of a thermoplastics material; (c) inserting the tube length in the mold mans with a portion thereof in the intermediate area and axial lengths confined in the tube retaining means in the axial lengths of the mold; (d) substantially filling the interior of the tube with a substantially incompressible fluid while closing off a first end of the tube; (e) increasing the temperature of the tube until at least the portion of the tube in the intermediate area reaches an elevated temperature range; (f) communicating the fluid in the interior of the tube with a source of said fluid at an end of the tube opposite the closed off end; (G) providing a predetermined quantity of said fluid in said source; (h) substantially instantaneously increasing pressure of the fluid interior of the tube to apply a high pressure spike by abruptly displacing said predetermined quantity from said source to said tube interior, and; (i) thereby expanding the portion of tube in the intermediate area while stretching and thinning the wall thickness of the expanded portion, and; (j) thereafter cooling the tube to maintain the resultant expanded intermediate section thereof.

23. The method of claim 22 wherein the greater diameter portion is formed as an enlarged cavity interior of the mold means intermediate the ends of the mold means.

* * * * *